United States Patent [19]

Kurkov et al.

[11] 4,000,185
[45] Dec. 28, 1976

[54] PROCESS FOR THE PRODUCTION OF 1,4-DIACYLOXY-2-BUTENE FROM BUTADIENE

[75] Inventors: Victor P. Kurkov, San Rafael; Seymour J. Lapporte, Orinda, both of Calif.

[73] Assignee: Chevron Research Company, San Francisco, Calif.

[22] Filed: Feb. 11, 1975

[21] Appl. No.: 548,931

[52] U.S. Cl. .......................................... 260/497 R
[51] Int. Cl.² ........................................ C07C 67/04
[58] Field of Search .............................. 260/497 R

[56] References Cited
UNITED STATES PATENTS 3,770,813  11/1973  Kollar ............................ 260/497 R

FOREIGN PATENTS OR APPLICATIONS 1,138,366  7/1948  United Kingdom .......... 260/497 A

*Primary Examiner*—Anton H. Sutto
*Assistant Examiner*—Michael Shippen
*Attorney, Agent, or Firm*—G. F. Magdeburger; John Stoner, Jr.; W. Keith Turner

[57] ABSTRACT

1,4-diacyloxy-2-butene useful as a diol precursor is produced by reacting butadiene with an alkali metal salt in the presence of iodine, iodine monochloride or iodine trichloride.

7 Claims, No Drawings

PROCESS FOR THE PRODUCTION OF 1,4-DIACYLOXY-2-BUTENE FROM BUTADIENE

BACKGROUND OF THE INVENTION

1. Field of the Invention

This application is concerned with the production of 1,4-diacyloxy-2-butene by the reaction of butadiene and an alkali metal salt in the presence of iodine, iodine monochloride or iodine trichloride. The compounds may be hydrogenated and hydrolyzed to form the 1,4-diols, which are useful precursors in the production of polyesters.

2. Description of the Prior Art

U.S. Pat. No. 3,770,813 discloses a process for producing 1,2-glycol esters by reacting monoolefins with a fatty acid, iodine, oxygen, and at least one alkali metal cation.

SUMMARY OF THE INVENTION

A process is provided for producing 1,4-diacyloxy-2-butene by reacting one mol of butadiene with at least 2 mols of an alkali metal salt of a lower fatty acid in the presence of at least 1 mol of $I_2$, $ICl$ or $ICl_3$.

The reaction is carried out at a temperature in the range of 50° to 200 °C, preferably from about 75° to 175° C. The reaction is preferably carried out under anhydrous conditions if the desired product is the 1,4-diacyloxy compound. The presence of even a small amount of water leads to the formation of substantial quantities of a 1,2-diacyloxy isomer.

The catalyst, preferably $I_2$, is employed in quantities of from about 1 to 2 mols relative to butadiene. However, it can be regenerated by oxidation, e.g., with air or oxygen, in a separate step.

Examples of the salts which may be employed are the sodium, lithium and potassium salts of acetic, propionic and butanoic acid. The acetates are preferred The amount of salt employed is preferably in substantial excess relative to the butadiene. Thus, it is preferred to use from about 3 to 6 mols of the salt per mol of butadiene.

In order to maintain anhydrous conditions so that high selectivity of the 1,4 isomer is retained, it is necessary to remove water of reaction as it forms. This is preferably accomplished by carrying out the reaction in the presence of a solvent which will remove the water as it forms. Examples of such solvents are aliphatic anhydrides such as acetic, propanoic and butanoic anhydride. Acetic anhydride is the preferred solvent.

The reaction will generally be carried out in about 1 to 24 hours, usually from about 4 to 16 hours. Hydrolysis of the diacyl compounds to produce the desired diol is accomplished by conventional methods, i.e., by basic hydrolysis with aqueous sodium hydroxide, etc.

Hydrogenation of the compounds in order to produce saturated diols may be accomplished either before or after hydrolysis. The use of any conventional hydrogenation technique is suitable.

In another embodiment of the invention, the halogen is employed in catalytic amounts, e.g., from about 1:5 to 1:1 mols relative to butadiene, and air or oxygen is used as an oxidant. Yields are somwhat lower than when the desired stoichiometric amounts are employed.

The following examples illustrate the processes of this invention. The examples are illustrative only, and are non-limiting.

EXAMPLES

Example 1

A 260-ml Fisher-Porter bottle provided with a magnetic stirrer was charged with:
83.3 g (1387 mmols) acetic acid
21.2 g (207 mmols) acetic anhydride
38.2 g (150 mmols) iodine
45.8 g (450 mmols) potassium acetate
5.7 g (100 mmols) 1,3-butadiene The reactor was sealed and placed in a 100° C oil bath for 16 hours. 2.4 g of unreacted butadiene was distilled out, corresponding to 57% conversion.

Chromatographic analysis showed 37 mmols or 62% yield of butene diacetates of the following composition:

| | |
|---|---|
| 1,2-diacetoxy-3-butene (A) | 18.2% |
| cis-1,4-diacetoxy-2-butene (B) | 19.7% |
| trans-1,4-diacetoxy-2-butene (C) | 62.1% |
| Total selectivity to the 1,4-isomer = 81.8% | |

EXAMPLES 2-11

The general procedure of Example 1 was followed, with the changes illustrated in Table I. 104 mmols of 1,3-butadiene was employed in each run. The products are indicated as A, B and C, as in Example 1 in each of the tables.

These experiments show the following:
Examples 1 and 2 show the effect of $I_2$ concentration.
Example 3 shows that lithium acetate gave 20% lower yield than potassium acetate.
Example 4 shows that ICl, which has less iodine per mol than $I_2$, is fully equivalent to $I_2$ as a reagent in the reaction.
Example 10 shows the detrimental effect of water. The yield decreased to 25% and the selectivity for the 1,4-isomer was only 41%.
Similarly, with copper diacetate instead of potassium acetate, the major product was 1,2-diacetoxy-3-butene (Example 11).

EXAMPLES 12-13

The procedure of Example 1 was followed, except that butadiene was continuously added at a rate of 1 cc/hr. Results are tabulated in Table II.

CATALYTIC ACETOXYLATIONS

Example 14

A 305-ml stainless-steel bomb was charged with:
106.9 g acetic anhydride
5.0 g (20 mmols) iodine
2.1 g (20 mmols) potassium acetate
6.1 g (113 mmols) 1,3-butadiene The bomb was sealed and pressured with 800 psig of air. The reaction was stirred magnetically in a 100° C oil bath for 8 hours. 1.4 g of unreacted butadiene was recovered, which corresponds to 78% conversion.

Gas chromatographic analysis showed the following products:

| | |
|---|---|
| 1-acetoxy-2-hydroxy-3-butene | 5.1% |
| 1,2-diacetoxy-3-butene (A) | 34.4% |
| unknown (D) | 5.9% |
| cis-1,4-diacetoxy-2-butene (B) | 11.9% |

-continued

| | |
|---|---|
| trans-1,4-diacetoxy-2-butene (C) | 42.7% | in a total yield of 14 mol percent. The selectivity for the 1,4-isomer was 54%.

EXAMPLES 15–17

The general procedure of Example 14 was followed with modifications and results shown in Table III. In Example 15, 50 ml each of acetic acid and acetic anhydride were employed as solvent. In Example 17, 80 ml of acetic acid and 20 ml of acetic anhydride were used.

These examples show the effect of solvent. The highest selectivity for the 1,4-isomer was obtained in acetic anhydride. Increasing amount of acetic acid relative to the anhydride decreased selectivity. Example 17 shows the effect of alkali metal acetate. Sodium acetate gave somewhat higher yield than potassium acetate. The selectivities were the same.

While the character of this invention has been described in detail with illustrative examples, this has been done by way of illustration only and without limitation of the invention. It will be apparent to those skilled in the art that modifications and variations of the illustrative examples may be made in the practice of the invention within the scope of the following claims.

We claim:

1. A process for the preparation of 1,4-diacyloxy-2-butene which comprises contacting one mol of butadiene with from about 2 to about 6 mols of an alkali metal salt of a lower fatty acid, in the presence of at least 1 mol relative to butadiene of a halogen selected from the group consisting of $I_2$, ICl, or $ICl_3$, the reaction being carried out under substantially anhydrous conditions at a temperature in the range from about 50° C to about 200° C for a period of from about ½ to about 24 hours.

2. The process of claim 1 in which the fatty acid salt is potassium or sodium acetate.

3. The process of claim 1 in which the halogen is employed in a molar amount relative to butadiene of from about 1:1 to 3:1.

4. The process of claim 1 wherein the reaction is carried out in the presence of a water-absorbing solvent.

5. The process of claim 4 in which the solvent is an anhydride of a lower aliphatic acid.

6. The process of claim 5 in which the anhydride is acetic anhydride.

7. A process for preparing 1,4-diacyloxy-2-butene which comprises contacting butadiene and an alkali metal salt of a lower fatty acid, in the presence of a catalytic amount of a halogen selected from the group consisting of $I_2$, ICl, or $ICl_3$, the reaction being carried out in the presence of acetic anhydride and an oxidant selected from the group consisting of air or oxygen.

* * * * *

TABLE I

Acetoxylation of Butadiene with Stoichiometric Quantity of Catalyst

| Ex. | Halogen | mmols | Salt | mmols | Time Hrs. | Conversion % | Yield % | Products, % A | B | C | Selectivity % 1,4 Isomers |
|---|---|---|---|---|---|---|---|---|---|---|---|
| 2 | $I_2$ | 50 | Potassium acetate | 300 | 15 | 49.8 | 54.6 | 12.4 | 20.9 | 66.7 | 87.6 |
| 3 | $I_2$ | 100 | Lithium acetate | 300 | 16 | 50.4 | 34.1 | 13.5 | 19.5 | 67.1 | 86.6 |
| 4 | ICl | 100 | Potassium acetate | 300 | 16 | 42.4 | 55.7 | 11.1 | 23.5 | 65.4 | 88.9 |
| 5 | $I_2$ | 100 | Potassium acetate | 300 | 16 | 59.6 | 55.4 | 17.3 | 17.6 | 65.0 | 82.6 |
| 6 | $I_2$ | 100 | Potassium acetate | 300 | 16 | 49.8 | 54.0 | 12.2 | 20.9 | 66.7 | 87.6 |
| 7 | $I_2$ | 100 | Potassium acetate | 300 | 4 | 37.2 | 52.0 | 11.9 | 21.4 | 66.6 | 88.0 |
| 8 | $I_2$ | 100 | Potassium acetate | 200 | 16 | 47.0 | 36.0 | 11.4 | 19.1 | 69.5 | 88.6 |
| 9 | $I_2$ | 100 | Sodium acetate | 300 | 16 | 61.0 | 44.0 | 6.8 | 20.4 | 72.8 | 93.2 |
| 10[1] | $I_2$ | 100 | Potassium acetate | 300 | 4 | 86.0 | 25 | 0 | 4.0 | 37.0 | 41.0 |
| 11[2] | $I_2$ | 50 | Copper acetate | 100 | 4 | 93.0 | 19 | 71.3 | 0 | 27.5 | 27.5 |

[1]556 mmol water added, 59 mol % of 1,2-dihydroxybutene produced
[2]1.1 mol % 1,2-butenediol produced

TABLE II

Acetoxylation of Butadiene with Continuous Butadiene Addition

| | Reactants | | | | Time | Conversion | Yield | Products, % | | | Selectivity |
|---|---|---|---|---|---|---|---|---|---|---|---|
| Ex. | Halogen | mmols | Salt | mmols | Hrs. | % | % | A | B | C | % 1,4 Isomers |
| 12 | $I_2$ | 100 | Potassium acetate | 300 | 16 | 26.5 | 48.3 | 14.6 | 18.5 | 66.8 | 85.3 |
| 13 | $I_2$ | 100 | Potassium acetate | 300 | 7.5 | 11.8 | 32.7 | 1.2 | 25.5 | 73.3 | 98.8 |

TABLE III

Catalytic Acetoxylation of Butadiene at 120° C

| | Reactants | | | | Time | Conversion | Yield | Products, % | | | | Selectivity |
|---|---|---|---|---|---|---|---|---|---|---|---|---|
| Ex. | Halogen | mmols | Salt | mmols | Hrs. | % | % | A | B | C | D | % 1,4 Isomers |
| 15 | $I_2$ | 20 | Potassium acetate | 20 | 8 | 89 | 22.7 | 66.5 | 6.7 | 26.8 | — | 33.5 |
| 16 | $I_2$ | 20 | Sodium acetate | 20 | 16 | 89 | 20.0 | 48.8 | 9.7 | 41.5 | — | 51.2 |
| 17 | $I_2$ | 20 | Potassium acetate | 40 | 16.5 | 90 | 19.9 | 49.1 | 11.9 | 32.2 | 6.8 | 44.1 |